United States Patent [19]
Yukov

[11] Patent Number: 5,361,767
[45] Date of Patent: Nov. 8, 1994

[54] TISSUE CHARACTERIZATION METHOD AND APPARATUS

[76] Inventor: Igor Yukov, 422 Old Country Rd., Orange, Conn. 06477

[21] Appl. No.: 8,604

[22] Filed: Jan. 25, 1993

[51] Int. Cl.$^5$ ............................................. A61B 8/00
[52] U.S. Cl. ............................................. 128/660.06
[58] Field of Search ..................... 128/660.06, 660.07, 128/660.04; 73/597, 599

[56] References Cited

U.S. PATENT DOCUMENTS

| | | | |
|---|---|---|---|
| 4,414,850 | 11/1983 | Miwa et al. | 128/660.06 X |
| 4,830,015 | 5/1989 | Okazaki | 128/660.06 |
| 4,982,339 | 1/1991 | Insana et al. | 128/660.01 X |

OTHER PUBLICATIONS

Parker, K. J. et al "Measurement of UTS Attenuation from Regions Selected from B-scan Images", IEEE Trans. on BME vol. BME-3 #8A, 1983, pp. 431–443.
Ophir, J. et al, "Attenuation Estimation in Reflection: Progress & Prospects," UTS Imaging 6, pp. 349-395 (1984).

*Primary Examiner*—Francis Jaworski
*Attorney, Agent, or Firm*—Bachman & LaPointe

[57] ABSTRACT

A method and apparatus for non-invasively determining a type of tissue and its state within a living entity are disclosed. The method includes the steps of using an imaging technique to generate an image of the tissue matter to be analyzed, selecting a region of interest on the image; positioning a device for transmitting ultrasonic signals at desired frequencies in a desired location relative to the tissue matter; transmitting ultrasonic signals at at least two different frequencies through the region of interest; detecting echo signals reflected by the tissue matter; and analyzing the echo signals to determine attenuation data for the tissue matter. The apparatus includes an imaging device for generating an image of the tissue matter to be analyzed, a device for selecting the region of interest, a device for transmitting ultrasonic signals, a receiver for detecting the echo signals, a display device for displaying the echo signals, and a computer for analyzing and calculating the attenuation data.

36 Claims, 4 Drawing Sheets

TISSUE CHARACTERIZATION METHOD AND APPARATUS

BACKGROUND OF THE INVENTION

The present invention relates to a method for non-invasively determining the type of tissue matter or the state of tissue matter in a living body. The present invention allows physicians and diagnosticians to determine the presence of healthy or unhealthy tissue and to determine a proper course of treatment. The method of the present invention is also helpful in allowing medical personnel to monitor the effects of treatments such as chemotherapy and X-ray therapy by measuring attenuation information in the affected organ.

In the medical field, especially in oncology, it is difficult to determine the nature of an internal anomaly in a non-intrusive manner. It is also difficult to detect abnormalities at early stages when treatment is most needed. Physicians often use the so-called "biopsy" method to find the presence of abnormal cells. This method requires finding a group of suspicious cells and obtaining little pieces of tissue containing these cells by inserting a needle into the patient's body. Often, the process has to be repeated several times in order to obtain samples from different suspicious spots. To improve the accuracy of this technique, the needle is often directed into the body under the guidance of an X-ray imaging machine or an ultrasound imaging device. For a patient, this can be a painful process because of its invasive nature. It can also be a dangerous process.

Ultrasound diagnostic methods have been used by physicians and diagnosticians to determine the presence of abnormalities in living human tissue. Existing ultrasound diagnostic methods utilize information obtained from sound signals reflected by the organ or tissue matter under examination.

In existing ultrasound diagnostic methods, there are generally two types of displays for examining reflected signals or echoes. One type of display is known as an A-mode display. In this display, each transmitted pulse triggers the sweep of an oscilloscope. Each pulse and the returning echoes are displayed as vertical deflections on the trace. The sweep is calibrated horizontally in units of distance. Vertically, the sweep shows the magnitude of the reflected signals in units of volts. In an A-mode display, the transducer is kept stationary so that any movement of echoes along the trace will be the result of moving targets.

The second type of display is known as the B-mode display. A B-mode display presents a two-dimensional image of a structure such as an organ of the body. In this case, the transducer is moved with respect to the body while the horizontal deflection of the oscilloscope is made to correspond to the movement of the transducer. The movement may be linear, circular or a combination of the two, but where it is anything other than linear, the sweep must be made to compensate for variations in order to provide a true two-dimensional display of the segment being scanned. The B-mode display system employs reflected signals. The magnitudes of the reflected signals are modulated in the oscilloscope scan through brightness.

Operators using a B-mode system know a normal echographic image of the structure of an organ being examined. If there are growths and/or abnormalities in the organ under examination, then the normal echographic B-scan image is different. So, for operators, it is relatively easy to find abnormalities through echographic B-scan images. There is however a big problem in determining what kind of abnormality, anomaly, tumor or growth is present using only a B-scan image.

According to the theory of the propagation of an acoustic wave, any media has its own acoustic absorption coefficient. Attempts have been made to diagnose the nature of abnormalities within the human body by using a combination of A-mode and B-mode imaging to obtain acoustic propagation information. These attempts have been unsuccessful because the intensity or magnitude of the reflected signals from boundaries of the structure of the tissue under examination depend not only on the acoustic characteristics of the tissue but also on the angle of the incident wave to the reflected surface, roughness of the reflected surface, and the geometry of the reflected surface.

Systems employing acoustic theories have been developed to acoustically determine the nature of tissue within a body. One such system is disclosed in USSR Patent No. 406,531 to Yukhananov. This system uses signals at two frequencies directed toward the surfaces or boundaries being examined to determine the attenuation information through a medium. When the desired attenuation data is determined, it is possible to assess the constituency or composition of the anomaly under investigation. This system is based on certain mathematical derivations and theorems which were identified in a paper entitled "Measurement of Ultrasound Attenuation In Vivo" by I. Yukhananov (Yukov) presented at a seminar of the Academy of Science of the USSR on "Electronic Apparatus in Medicine" in Moscow in 1970, in an article entitled "Substantiation of a Method for Measuring Ultrasonic Absorption in Tissues" by I. Yukov et al. in *News of Medical Instrumentation*, Moscow, 1971 and in an article appearing in the *Proceedings of the Third Oncology Conference of Estonia, Latvia and Lithuania*, entitled "A New Method of Ultrasonic Differential Diagnosis of Breast Tumors" by I. Yukov et al. These materials illustrate the generation of attenuation data for analyzing materials under investigation. The two-frequency method discussed in those papers has been extensively used. Such systems as that mentioned in Russian Patent No. 406,531 have had limited success. One of the reasons is that the device disclosed therein is based on only A-mode display information.

It is known that soft tissues frequently contain multiple layers. If the normal tissue or a tumor is homogeneous, then the echo signals can be recorded from the front and rear boundaries. If the normal tissue or tumor are not homogeneous, then there are additional signals from the interfaces of the layers. As is known, different layers can have different types of tissue which means different attenuation data according to the type of tissue. Using only A-mode visualization, it is sometimes very difficult to determine from what part of the investigated normal tissue or from what part of the tumor data is obtained. Moreover, the data is often from several layers, although it looks like it is from only one layer. This happens because the boundaries of the layers in many cases are not parallel and one signal can be overlooked because of its weakness. In these cases, the data becomes mixed and could lead to diagnostic mistakes. This is why some prior art techniques require the operator to calculate a lot of layers, which is quite time consuming, in order to ensure that data is being taken from a desired layer and from the proper region of the examining organ.

In addition to the aforementioned Russian patent, U.S. Pat. No. 4,202,215 to Meyer discloses a system for determining attenuation coefficients of tissue. This patent discusses several technical papers on the topic as well as the inadequacies of methods such as that proposed in U.S. Pat. No. 4,057,059 to Hill. The system disclosed in the '215 patent senses when the returning echoes are "white" and then calculates the attenuation coefficient of the tissue segment which causes the return echoes to be "white". As defined by the patentee, "white" means a sonic pressure pulse echo which has a substantially uniform spectrum amplitude at all frequency components of the echo. This system was contrasted with the measurement of peak echo amplitudes at two different frequencies as discussed in the system disclosed in the '049 patent.

U.S. Pat. No. 4,414,850 to Miwa et al. describes a method which is based on the theory and mathematics published by Yukov in 1970 and 1971. The method described in said patent for measuring characteristics of attenuations of domains in an object comprises transmitting ultrasonic waves into the object and receiving ultrasonic waves reflected from the object. The measured characteristics of attenuation of reflected waves is determined using signal intensities. In particular, a plurality of ultrasonic waves having different frequencies are transmitted either simultaneously or alternately to an object and the reflected waves are received from the object. The signal intensities corresponding to the transmission frequencies among the reflected waves are stored and the signal intensity ratio is calculated. The signal intensity ratio indicates the attenuation characteristic. The attenuation coefficient can also be obtained using a time interval from the transmission time to the time of the reflected wave is received. The attenuation slope can be obtained from this attenuation coefficient and the frequency difference between transmitted ultrasonic waves.

In later patents, U.S. Pat. Nos. 4,452,082, 4,509,524, 456,019 and 4,575,799, Miwa et al. disclose a dissatisfaction with the technology in the '850 patent and improvements thereto. In the '799 patent, Miwa et al. admit that, in the previous methods, the assumption that reflected signals are not frequency dependent is wrong. Miwa et al. also admit that their three frequency method is impossible to apply because of "errors due to local fluctuation of the spectrum" and other reasons connected with too many complications needed to get correct information.

It should be noted that the method set out in the '799 patent is impractical. In that method, a plurality of transducers with different frequency bandwidths are used to obtain the normalized power frequency spectrum for the measured data. Practically, this is impossible methodologically and technically, it is complicated.

U.S. Pat. No. 4,676,251 to Bernatets illustrates an improvement to the apparatus disclosed in U.S.S.R. Patent No. 406,531. The Bernatets patent discloses a device for the scanning of media by means of ultrasound echography comprising at least one ultrasonic transducer which is associated with a transmitter stage and with a receiver stage which comprises a conventional first processing circuit and a second processing circuit which is connected parallel thereto and which comprises a series connection of a circuit for automatic gain control as a function of the distance of the echoes, a heterodyne circuit, and n parallel channels, each of which comprises a series connection of a circuit for the correction of diffraction effects, a filter for selecting a narrow frequency band from the pass-band of the transducer, a logarithmic amplifier and a divider whose output is connected to one of the n inputs of a circuit for determining values whose output is connected to the display device provided in the first processing circuit.

As mentioned above, it would be very difficult to use two frequency method only as A-mode image information. Inaccuracies are, in part, due to the fact that soft tissue in the body contains numerous layers. If the tissue contains abnormalities such as a tumor, then on the A-mode display would appear reflections caused by the presence of the tumor. The tumor may in turn contain layers of tissue, or it may be homogeneous (in which case the reflected signals displayed in the A-mode should be such showing only the front and rear boundaries of the tumor). However, if the tumor is not homogeneous, then additional signals will be presented from various layers or interfaces in the tumor itself. As is known, different layers in tissue and tumors means different types of tissue throughout the depth of the ultrasonic examination. These different types of tissues have different attenuation coefficients of ultrasonic energy dependent on tissue type. Thus, the A-mode presentation of reflections from an ultrasonic examination has proven difficult in use and in determining what part of the tissue or tumor is being presented. The situation is further complicated by the fact that the tissue/interface boundaries themselves are not straight lines, but are irregular in shape and by the fact that they may be closely spaced to each other so that data presented in the A-mode may be for more than one interface and could consist of non-objective information. To obtain correct or objective tissue information and accurate attenuation data for diagnostic purposes, the '251 patent has the same difficulties as the aforementioned Russian patent.

U.S. Pat. No. 4,546,772 to Flax measures the attenuation information in a human body through spectrum analyses of reflected signals by using a phase locked loop. This method has all the problems previous discussed. Many people have tried to use spectrum analysis to find attenuation information but have not been successful.

U.S. Pat. No. 4,597,292 to Fujii et al., U.S. Pat. No. 4,644,510 to Fujii and U.S. Pat. No. 4,646,748 to Fujii et al. all measure attenuation information in the human body by using two or more frequencies. Like Miwa et al., Fujii et al. suggest making a plurality of scanning lines to obtain the attenuation information. This is practically very difficult or even impossible because one can not get the same profile several times.

SUMMARY OF THE INVENTION

It is an object of the present invention to provide a non-invasive diagnostic method which overcomes the aforementioned problems.

It is a further object of the present invention to provide a non-invasive diagnostic method as above and an apparatus which enables physicians and other medical technicians to accurately determine a type of tissue undergoing examination and the state of that tissue.

It is still a further object of the present invention to provide a non-invasive diagnostic method and apparatus as above wherein imaging techniques and multiple frequency techniques are used together to determine the type of tissue undergoing examination and its state.

These and other objects and advantages will become more apparent from the following description and drawings wherein like reference numerals depict like elements.

In accordance with the present invention, the method for non-invasively determining a type of tissue or the state of a tissue broadly comprises the steps of: using an imaging technique to generate an image of the tissue matter to be examined or an organ containing that tissue matter; selecting a region of interest on said image representative of said tissue matter to be analyzed; positioning a device for transmitting an ultrasonic signal at a desired frequency in a desired location relative to the tissue matter to be analyzed; transmitting a first ultrasonic signal at a first frequency through the selected region of interest; transmitting a second ultrasonic signal at a second frequency through the region of interest; detecting echo signals at the first and second frequencies reflected by the tissue matter; and analyzing the echo signals to determine at least one attenuation coefficient for said tissue matter.

The method of the present invention may be performed using an apparatus which includes a B-mode imaging device for creating a two-dimensional image of the tissue matter to be examined or an organ containing that tissue matter, a signal generator for generating ultrasonic signals at desired frequencies and in desired forms, and means for analyzing echo signals so as to determine at least one attenuation coefficient for the tissue matter. In a first embodiment of the present invention, the analyzing means includes a visual display means such as an A-mode device. In a second embodiment, the analyzing means comprises a computer for automatically calculating the attenuation coefficient(s).

Details of the method and apparatus of the present invention are set forth in the following detailed description and the accompanying drawings wherein like reference numerals depict like elements.

DETAILED DESCRIPTION

Figure 1:
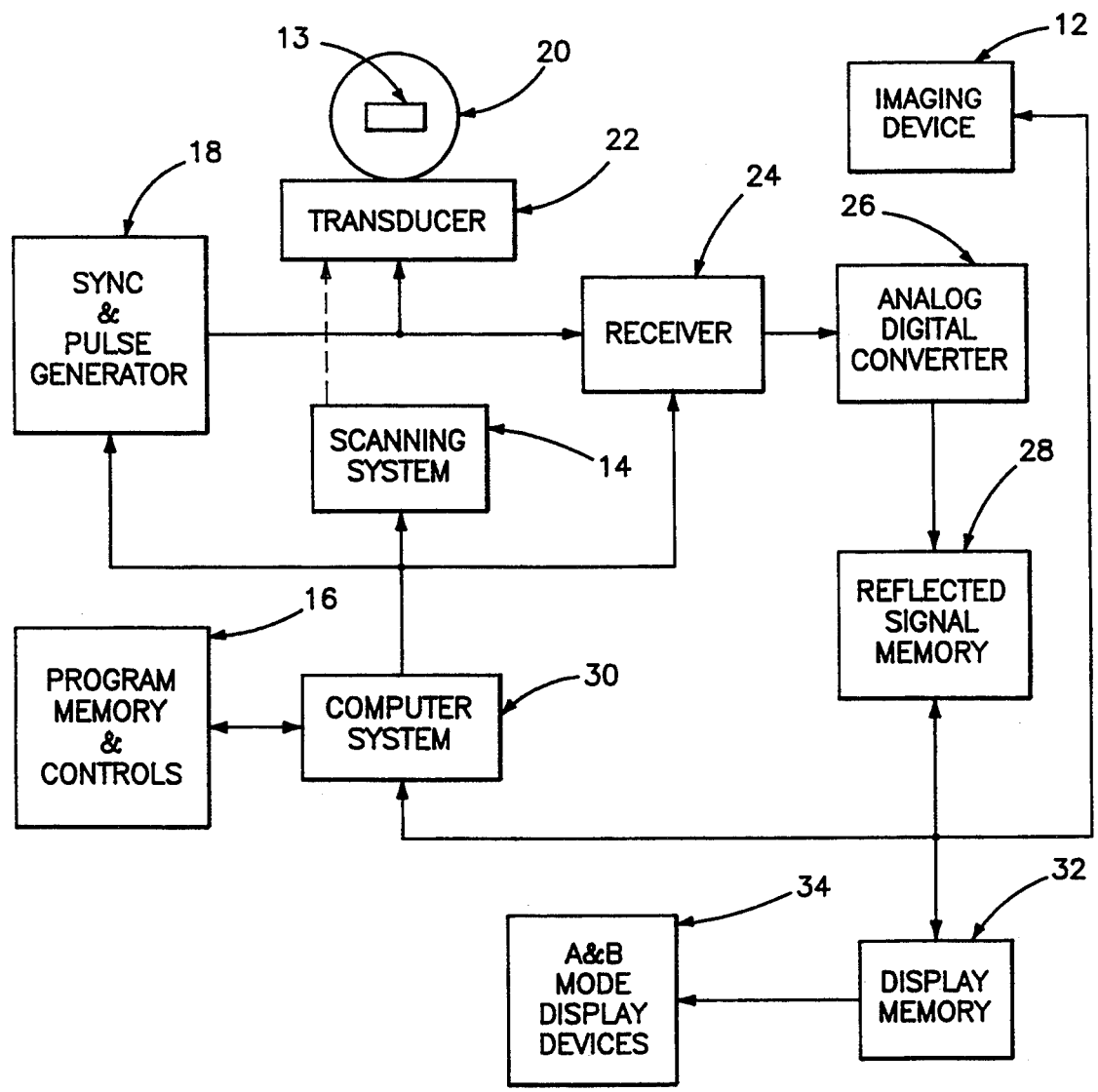
FIG. 1 is a schematic representation of an apparatus which can perform the method of the present invention.

Referring now to the drawings, FIG. 1 illustrates an apparatus for performing the method of the present invention. The apparatus 10 comprises a system for manually and/or automatically analyzing tissue matter to ascertain the nature of the tissue and/or its state by determining the attenuation coefficient or coefficients of the tissue matter. The manner in which the apparatus 10 is used, as will be described in more detail hereinafter, is determined by the specific frequencies used to perform the method.

The apparatus 10 as shown in FIG. 1 includes a device 12 for providing an image of a target 13 containing the tissue matter to be analyzed. The target may be an organ containing the tissue matter, a tumor, or some other mass within a patient 20. The imaging device 12 may comprise any conventional imaging device known in the art. In a preferred embodiment of the present invention, the device 12 comprises a B-mode (2-dimension) imaging device.

A display device 34 and a control panel unit 16 are connected to the imaging device 12 to allow an operator to see an image of the tissue matter or the organ containing the tissue matter and to pick out regions of interest for further exploration. The display device 34 may be any suitable device known in the art such as a CRT tube. The control panel unit 16 may include any suitable means known in the art for allowing an operator to select regions of interest on the image. For example, the control panel may include means for positioning digital calipers against the image to measure the size, depth and/or thickness of the tissue matter under investigation, means for adjusting image quality factors such as contrast and brightness, means for defining region(s) of interest using cursers or X-Y pointers and means for increasing the magnification of such region(s) of interest.

The apparatus 10 further includes means 18 for generating ultrasonic signals at desired frequencies and with a desired shape and transducer/receiver means for directing the signals at the target 13 and for receiving echo signals reflected by said tissue matter under examination and/or said organ containing said tissue matter. The ultrasonic signal generating means 18 may comprise any suitable pulse generator known in the art capable of generating ultrasonic signals at discrete frequencies, as signal pairs having two different frequencies, and/or as broad-band signals containing desired frequencies. If desired, the pulse generator 18 may also be used to generate the ultrasonic pulses used by the imaging device 12 to create an image of the tissue matter to be analyzed or the organ containing said tissue matter.

The transducer/receiver means may comprise any suitable transducer 22 and receiver 24 known in the art. For example, the transducer 22 may be a mechanical scanner, a linear scanner, or a phase-array scanner. The transducer 22 is acoustically coupled to the patient 20 by placing the transducer in contact with the patient at a desired location relative to the target and is used to transmit ultrasonic pulses through the patient. If desired, the transducer 22 may be used to transmit the ultrasonic pulses used by the imaging device 12.

As is known in the art, ultrasonic pulses transmitted through a human body generate echo pulse returns as the ultrasonic pulses contact structural material within the patient, tissue matter, and/or boundaries or interfaces within the tissue matter contacted by the pulses. The echo pulse returns thus generated are detected by the receiver 24. If desired, the receiver 24 may contain means (not shown) for amplifying the amplitude of the pulse returns and may be connected to the control panel 16 to allow an operator to amplify the pulse returns in any desired manner.

Typically, the receiver 24 receives the echo signals in analog form. An analog-to-digital (A/D) converter 26 is provided to digitize the analog echo signals. A storage device 28 is provided to store the signals in either digital or analog form. The converter 26 and the storage device 28 may comprise any suitable conversion and storage devices known in the art.

As previously mentioned, the apparatus 10 has a manual mode of operation and an automatic mode of operation. The manual mode is used when the frequencies of the ultrasonic pulses transmitted into the regions of interest are more than about 2% apart. In the manual mode, signals reflected back by the tissue matter and/or the organ being analyzed are received by the receiver 24 and visually displayed on a device 34. The display device 34 includes an A-mode display device on which at least two signals may be simultaneously displayed with at least one signal having a "+ polarity" and at least one other signal having a "− polarity". The polarity assigned to each signal may be done by means known in the art associated with the display device. For example, the signals may be processed by computer software to omit certain phases or one of the signals may be inverted.

The signal(s) received by the display device 34 from the receiver 24 may be in either analog or digital form. If necessary, the signal(s) may be amplified by an operator using the control panel 16 and amplification means (not shown) within the receiver 24. If needed, means (not shown) may be provided to filter out unwanted noise from the signal transmitted to the device 34. The filter means may comprise any suitable filter known in the art. In the manual mode, the echo returns are visually displayed to the operator on the device 34 and, as explained hereinafter, are examined for certain criteria. The display presented to the operator may be a color image, an overlay, or a numerical display. The display device 34 may comprise any suitable device or arrangement for presenting the A-mode display alongside a B-mode image.

The automatic mode is used when the frequencies of the ultrasonic pulses transmitted into the regions of interest are less than about 2% apart. In the automatic mode, the reflected signals are transmitted in digital form to a computer 30 and a memory portion associated with the panel unit 16 for automatic processing and analysis of the signals. The manner in which the computer 30 and the program within the aforesaid memory portion processes and analyzes the signals will be discussed hereinafter.

Figure 2:
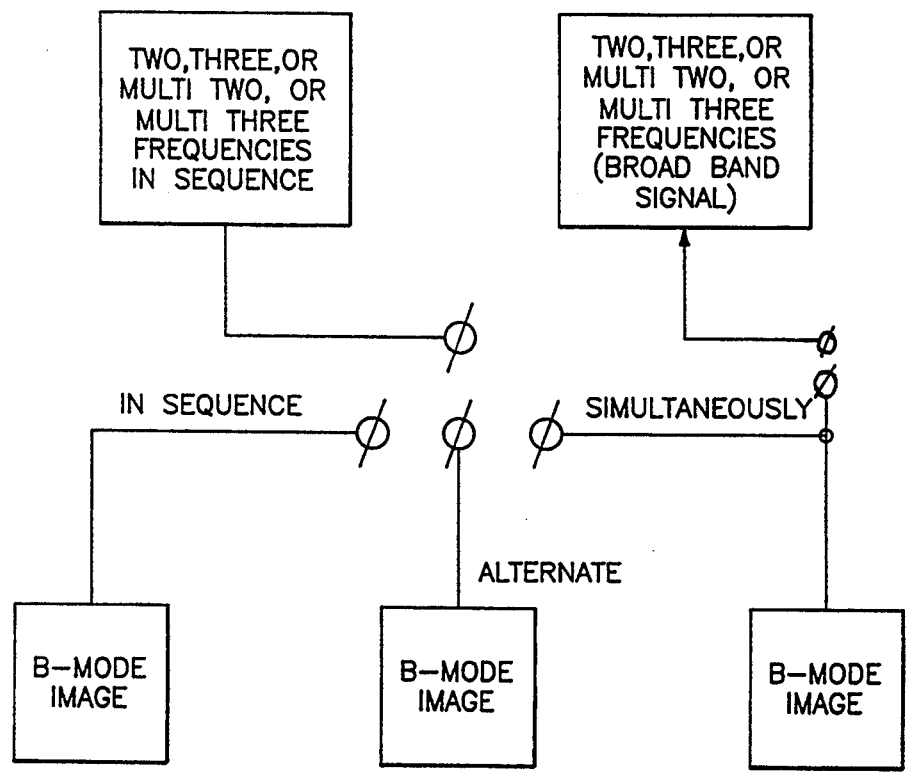
FIG. 2 is a schematic representation of a portion of the apparatus of FIG. 1.

FIG. 2 schematically illustrates certain switching arrangements available to the operator as part of the control panel unit 16. The switching arrangements allow the operator to use the apparatus in different modes. For example, the pulse generator 18 and transducer 22 may be used to generate two frequencies ($f_1$, $f_2$) in sequence or multiple pairs of frequencies ($f_1$, $f_2$ .. . $f_n$, $f_{n+1}$) in sequence. Using the switching arrangement shown in FIG. 2, the operator may select one of these pulse generation modes and use it with either simultaneous, sequential or alternate B-mode imaging. Preferably, the B-mode imaging is performed simultaneously with the transmission of the pulse waves used to generate the echo returns so as to avoid errors caused by breathing or movement of the patient.

FIG. 2 illustrates a mode wherein the pulse generator generates frequencies as broad-band signals. In this mode of operation, the operator has the choice of performing B-mode imaging simultaneously with either two frequencies ($f_1$, $f_2$) or multiple pairs of a desired set of frequencies including frequencies ($f_1$, $f_2$) which could be separated from broad band signals through Fast Fourier transform or by other means known in the art.

Figure 3:
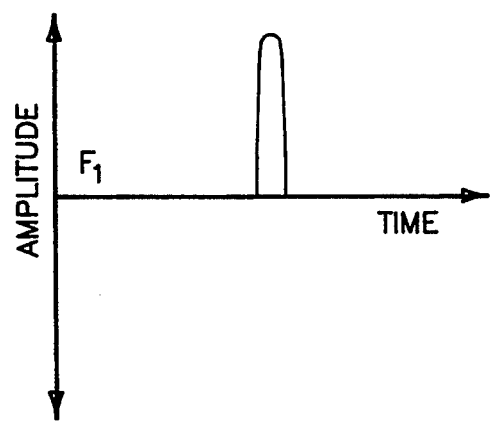
FIG. 3 illustrates a portion of an ultrasonic pulse wave introduced into the body of a patient.

It is known that a pulse emitted from an ultrasonic transducer such as the transducer 22 has a specific shape and width. FIG. 3 shows the characteristics of a typical pulse wave in monopolarity visualization. It is also known that when this pulse is reflected by the interface of media having different acoustic properties, its shape, width and amplitude will be altered by the geometry of the interface. If the interface surface is flat and perpendicular to the incident pulse, the reflection signal or echo will have the same shape and width as the original pulse.

Variations in the surface or angle of incidence will affect the shape and width of an echo signal. Thus, the amplitude of an echo signal depends not only on the surface geometry and the angle of incidence, but also on acoustic properties such as the acoustic impedance of the adjacent media and the attenuation coefficients. For example, if the acoustic impedance of a first layer closer to the transducer is less than the acoustic impedance of a second layer further from the transducer, the echo amplitude from the second layer can be larger than if the first layer had an acoustic impedance greater than that of the second layer. Attenuation coefficients affect the amplitude of the echo by decreasing both the amplitude of the original ultrasonic pulse before it meets the boundary of the two layers and also the amplitude of the echo as it returns. Tissue matter and the state of tissue matter may be determined by measuring attenuation coefficients.

Figure 4:
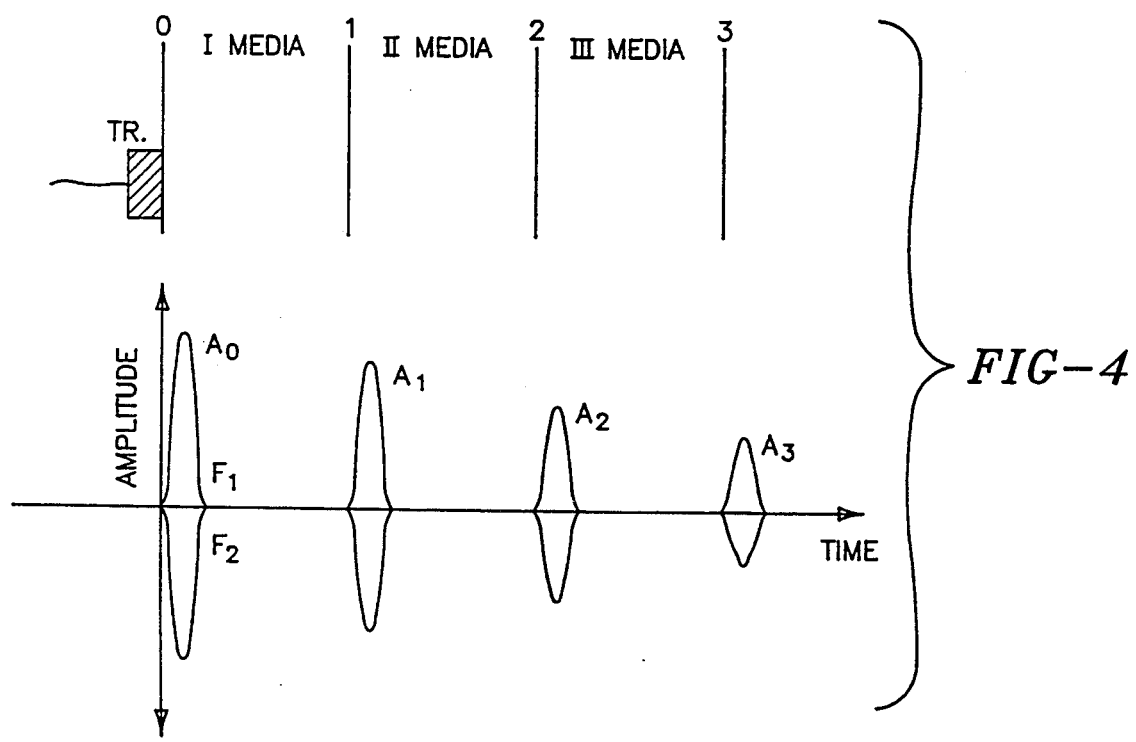
FIG. 4 illustrates a portion of a target having multiple layers being examined by an ultrasonic pulse wave and an echo return pulse wave generated as the pulse wave moves through said target.

A complex set of echoes are generated by an ultrasonic pulse as it propagates through a complex media such as soft tissues within a human body. Echoes return from each structure within the body as well as from layers within each structure. These layers exhibit a complex set of surface geometries and acoustic properties, particularly attenuation coefficients. A single anomaly, such as a tumor, may have many layers with different attenuation coefficients. If one measures the attenuation coefficient between the echoes from the front and rear boundaries, the result will be the average of the attenuation coefficients of all the layers within the tumor. The layers within the tumor may be different types of tissue with their own attenuation coefficients. FIG. 4 illustrates a typical effect on the measured attenuation coefficient when a structure or tissue matter has many different layers.

It is important for an operator to understand the structure of the tissue matter or organ under examination; that is to know which layer within the tissue matter or organ is being measured. The B-mode image display preferably used in the apparatus 10 allows an operator to judge the depth of various layers in the tissue matter being analyzed and thus helps the operator to identify the pulses in the echo returns.

In accordance with the present invention, the ultrasonic transducer 22 is used to direct ultrasonic pulses at different frequencies at the regions of interest and a receiver 24 is used to capture the return signals or echoes. As previously discussed, the ultrasonic pulses may be transmitted at the same time that the two dimensional (B mode) imaging is being performed or may be transmitted subsequent to or alternately with the two dimensional imaging step. In fact, the ultrasonic pulses used to generate the B-mode image may be transmitted by the transducer 22.

In one mode of operation, the ultrasonic transducer 22 transmits two pulse signals toward the target or region of interest with the first signal having a frequency $f_1$ and the second signal having a frequency $f_2$. The frequencies $f_1$ and $f_2$ may be any desired frequencies. The two pulses may be transmitted sequentially or simultaneously.

Figure 5:
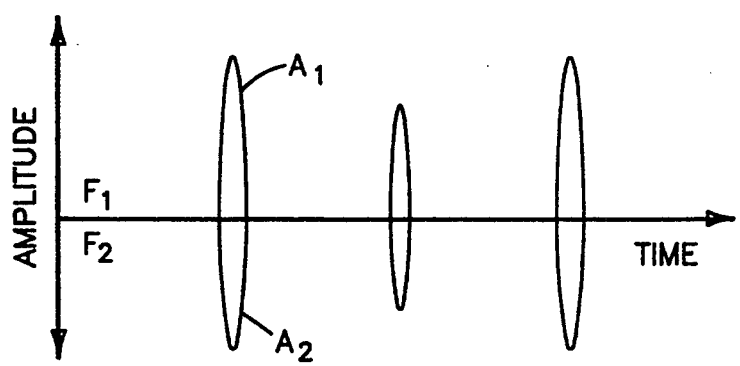
FIG. 5 illustrates a display of two echo pulse waves generated at different frequencies, one having a "+ polarity" and the other having a "− polarity"

As mentioned above, the receiver receives the echoes from the tissue matter under investigation. If the frequencies $f_1$ and $f_2$ are more than about 2% different, the echo signals $A_1$ and $A_2$ in either digital or analog form are transmitted to the visual display device 34 where they are displayed simultaneously. While there are various techniques for simultaneously displaying two echo signals, it is preferred that the signal $A_1$ be displayed for example as a signal having a "+ polarity" and the signal $A_2$ be displayed for example as a signal having a "− polarity" as shown in FIG. 4. FIG. 5 illustrates a typical signal display on the device 34. As can be seen from this figure, each signal has pulses at different amplitudes at specific times. Additionally, each individual pulse has a specific amplitude, width and shape.

When the signals are displayed on the device 34, they are initially visually examined to see whether the amplitudes of the return signals are sufficiently high. If the amplitudes of the signals being analyzed are too low, the operator can try to increase them by changing the angle of the transducer. If this is insufficient then the operator may maximize them using either the amplification means within the receiver 24 or such other amplification means not shown as may be provided in the apparatus 10. Appropriate means may be provided on the control panel 16 to allow the operator to increase the amplitude of the signals. If the amplitude of the signals cannot be maximized for some reason, the operator can choose to cause the pulse generator 18 to generate two new pulses at two new frequencies or analyze the existing echo pulses.

Figure 6:
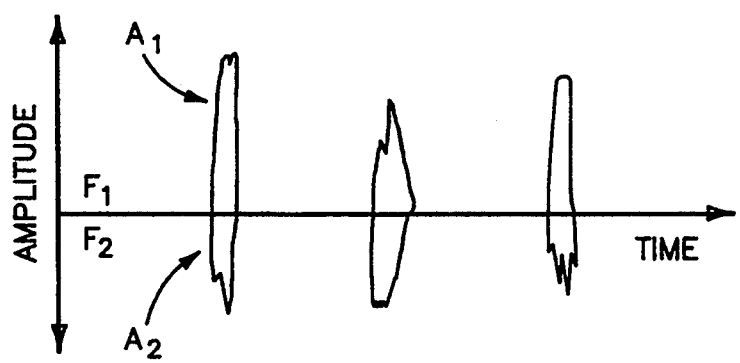
FIGS. 6 and 7 illustrate unacceptable forms of multifrequency echo pulse waves.
Figure 7:
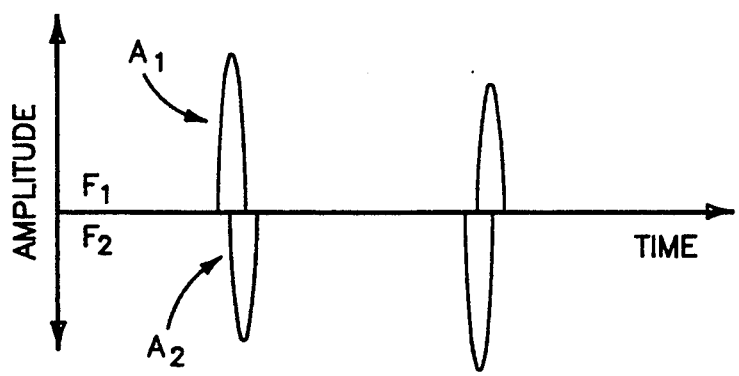

Assuming the amplitude of the signals to be satisfactory, the signals displayed on the device 34 are then visually examined to determine whether the pulses are aligned in terms of time, whether the individual pulses have any shape irregularities, and whether the individual pulses have similar widths. If the pulses are misaligned (as shown in FIG. 7), have shape irregularities (as shown in FIG. 6), or have width variations (as shown in FIG. 7), they should not be used to determine the attenuation coefficient(s). In that event, the operator can choose to change the position of the transducer relative to the patient and the target 13 and generate signals at the same frequencies $f_1$ and $f_2$. Alternatively, the operator can choose to change the frequencies $f_1$ and $f_2$ as well as the position of the transducer. After the operator changes the position of the transducer and/or changes the frequencies, the echo pulses are examined as before.

If the amplitude of the pulses is satisfactory and if the pulses are aligned and have no irregularities, then the echo pulse waves may be used to determine the attenuation coefficient(s) because the likelihood of error is minimal. If $I_m(f_1)$ is an intensity of a reflected signal from M layer for frequency $F_1$ and $I_{m+1}$ is an intensity of a reflected signal from M+1 layer with attenuation coefficient of $\alpha(f_1)$ between these two interfaces (boundaries), then according to acoustic propagation property it can be written $$I_{m+1}(f_1) = I_m(f_1) \cdot \exp/-2l\alpha(f_1) \tag{1}$$

where l is a distance between the M and M+1 layers. The same equation could be written for frequency $f_2$:

$$I_{m+1}(f_2) = I_m(f_2) \cdot \exp/-2l\alpha(f_2) \tag{2}$$

Equations (1) and (2) can be written if there are conditions of frequency independency of reflected signals from reflected interfaces (boundaries).

After division of equation (2) into equation (1) we can write:

$$\frac{I_{m+1}(f_2)}{I_{m+1}(f_1)} = \frac{I_m(f_2)}{I_m(f_1)} \cdot \exp/-2l(\alpha(f_2) - \alpha(f_1)) \tag{3}$$

After simplification and logarithmic conversion to Db we can write:

$$\beta = \alpha(f_2) - \alpha(f_1) = \frac{N_2 - N_1}{2l} \frac{Db}{CM} \tag{4}$$

where $\beta = \alpha(f_2) - \alpha(f_1) =$ differential attenuation coefficient between frequencies $f_2$ and $f_1$ and $N_2$ and $N_1$ are ratios of magnitudes of reflected signals from front and rear boundaries in Db on frequencies $f_2$ and $f_1$ accordingly.

For the computer, the equation (4) can be written in different ways, one of them is:

$$\beta = \frac{A_i(f_2) - A_{i+1}(f_2) - A_i(f_1) + A_{i+1}(f_1)}{2l} \tag{5}$$

where $A_i(f_2)$, $A_{i+1}(f_2)$ and $A_i(f_1)$, $A_{i+1}(f_1)$ are the magnitudes of the reflected signals at frequencies $f_2$ and $f_1$ accordingly in Db from layers i and i+1, l is the distance between signals $A_i$ and $A_{i+1}$ which is calculated as:

$$l = v \cdot t = 0.15 \cdot t cm \tag{6}$$

where v is the velocity of ultrasonic waves in tissue and which is equal approximately to 0.15 cm/$\mu$sec $\pm 5\%$; and t is the time of the ultrasonic waves propagation between the boundaries i and i+1.

In another way, the equation (4) can be written for computer through ratio of magnitudes of reflected signals.

In another mode of operation of the apparatus of the present invention, the transducer 22 is used to transmit three ultrasonic pulse signals at three different frequencies to the target 13. The signals may be at discrete frequencies ($f_1$, $f_2$, and $f_3$) or they may be separated from one broad-band signal. In the latter mode, the receiver 24 receives broad-band echo pulses which can be separated into the three frequencies $f_1$, $f_2$, and $f_3$ by Fast Fourier Transforms or by any other means known in the art. If the three frequencies, are more than about 2% different, then the echo signals are again transmitted to the display device 34.

The three pulse signals transmitted to the display device 34 may be displayed in a number of different ways. For example, the three pulses may be displayed simultaneously with one of the pulse waves superimposed over one of the other pulse waves and colored so as to distinguish it from the pulse wave over which it is superimposed. Alternatively, the echo pulse waves may be displayed in "+ − polarity, − polarity" pairs $f_1$, $f_2$, $f_1$, $f_3$, and $f_2$, $f_3$. As before, the pulse waves are visually examined to determine if the amplitude is sufficient, if the pulses in the waves are aligned in time, if the pulse in the waves have irregular shapes, and if the pulses in the waves have the same width. If the pulses waves have sufficient amplitude and have pulses aligned in time without irregularities and with substantially the same pulse widths, the echo signals may be used to determine the exponent of attenuation coefficient(s) for the tissue matter being examined and then to find an attenuation coefficient.

The following formula is well known in classical physics and relates the attenuation coefficient of any kind of wave with a natural law of attenuation:

$$\alpha(f_n) = K\alpha_o f_n^x \tag{7}$$

where $\alpha(f_n)$ = the value of the attenuation coefficient at $f_n$ frequency;
where $\alpha_o$ = the value of the attenuation coefficient at a unit frequency (one megahertz for example);
where X = exponent of the attenuation coefficient or the mathematical statement of the relationship between attenuation coefficient and frequency;
and K = a proportionality constant.

Assume that the object is examined by three frequencies: $f_1$, $f_2$, $f_3$, with $f_3 > f_2 > f_1$.

According to formula (7) we can write:

$$\begin{aligned} \alpha(f_1) &= K\alpha_o f_1^x \\ \alpha(f_2) &= K\alpha_o f_2^x \\ \alpha(f_3) &= K\alpha_o f_3^x \end{aligned} \tag{8}$$

Then the differential attenuation coefficients from (8) can be written as:

$$\begin{aligned} \beta_{31} &= \alpha(f_3) - \alpha(f_1) = K\alpha_o f_3^x - K\alpha_o f_1^x = K\alpha_o(f_3^x - f_1^x) \\ \beta_{32} &= K\alpha_o(f_3^x - f_2^x) \\ \beta_{21} &= K\alpha_o(f_2^x - f_1^x) \end{aligned} \tag{9}$$

And finally, the ratio of the differential attenuation coefficient can be written as:

$$\frac{\beta_{31}}{\beta_{21}} = \frac{f_3^x - f_1^x}{f_2^x - f_1^x} \tag{10}$$

$$\frac{\beta_{32}}{\beta_{21}} = \frac{f_3^x - f_2^x}{f_2^x - f_1^x}$$

$$\frac{\beta_{31}}{\beta_{32}} = \frac{f_3^x - f_1^x}{f_3^x - f_2^x}$$

At the same time, according to the two-frequency method, we can write the ratio of differential attenuation coefficient for the same three frequencies ($f_1$, $f_2$, $f_3$) between each two frequencies through amplitude data by using formula (4):

$$\frac{\beta_{32}}{\beta_{21}} = \frac{N_3 - N_2}{N_2 - N_1}; \tag{11}$$

$$\frac{\beta_{31}}{\beta_{21}} = \frac{N_3 - N_1}{N_2 - N_1}$$

$$\frac{\beta_{31}}{\beta_{32}} = \frac{N_3 - N_1}{N_3 - N_2}$$

Comparing the equations (11) and (10) we can write:

$$\frac{N_3 - N_2}{N_2 - N_1} = \frac{f_3^x - f_2^x}{f_2^x - f_1^x} \tag{12}$$

Equation (12) shows that if the ratio of any two reflected signals from any layer of the object at three frequencies and the value of the applied three frequencies is known, then it is possible to find the relationship between attenuation and frequency that is the exponent of attenuation. So, the general formula for attenuation coefficient for unit frequency can be written as:

$$\alpha_o = \frac{\beta_{nm}}{f_n^x - f_m^x} \tag{13}$$

where $\alpha_o$ = attenuation coefficient at unit frequency (one megahertz for example). Then the attenuation coefficient for any frequency is:

$$\alpha(j) = \alpha_o f(j)^x$$

where f(j) = value of any frequency.

Thus, using three frequencies for examining any object, it is possible to determine the attenuation coefficient and exponent of it (x). These parameters provide important information for establishing the object's property and its state. The determination of "x" and "α" does not require the knowledge of the distance between the layers, which is important and can be applied in different fields where it is difficult to find a distance between two interfaces.

Figure 8:
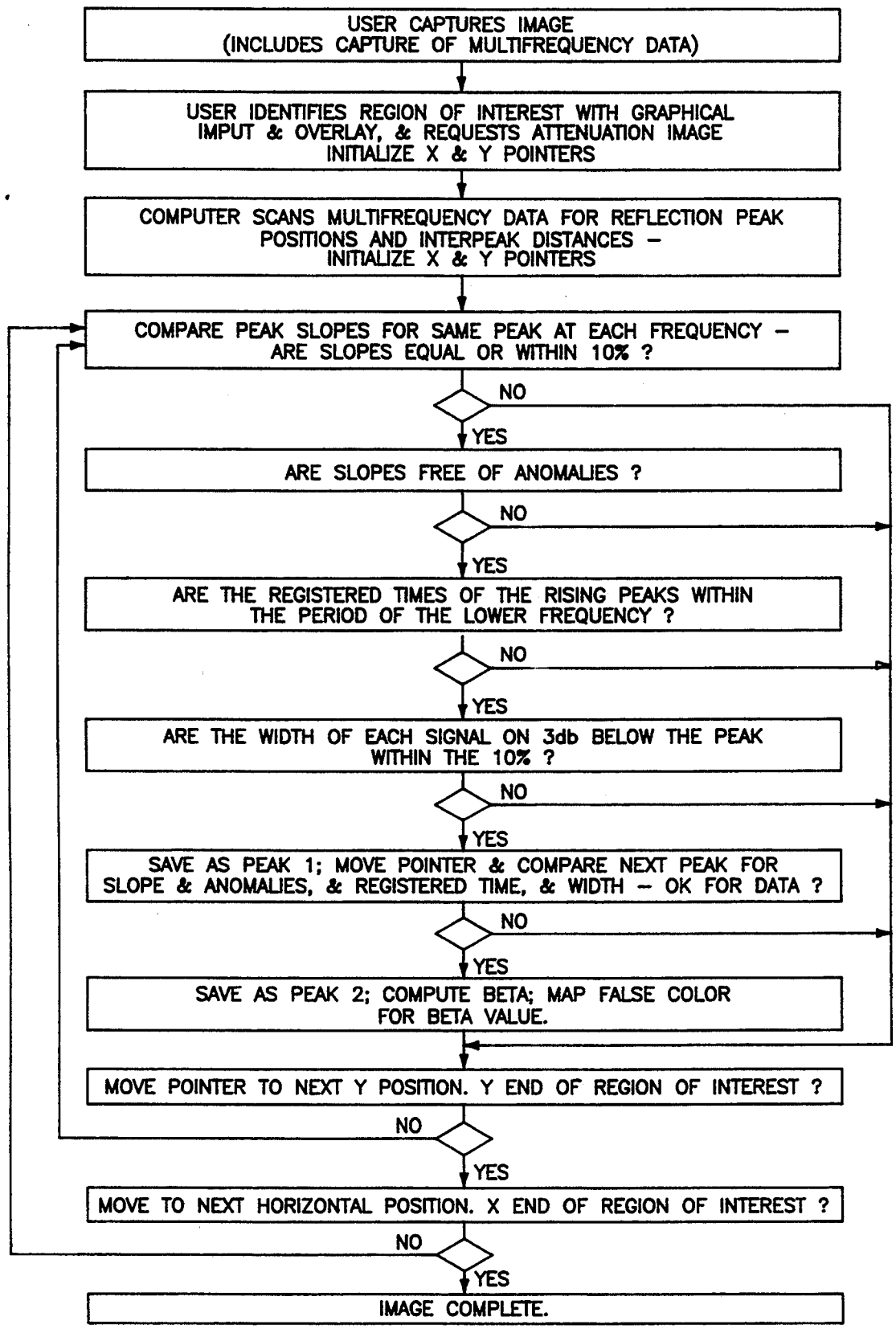
FIG. 8 illustrates a flowchart for operating the apparatus of the present invention and performing the method of the present invention in an automatic mode.

If the frequencies used to obtain the attenuation information are less than about 2% apart, then the exponent of the attenuation coefficient(s) and the attenuation coefficient(s) for the tissue matter being analyzed may be determined automatically. In this automatic mode, the echo signals received by the receiver 24 are converted into digital frequency data signals, stored in the memory device 28 and transmitted to the computer 30 and the program memory in unit 16 for analysis and determination of the attenuation coefficient(s). FIG. 8 illustrates the manner in which the information transmitted to the computer 30 and the program memory 16 is processed.

As shown in FIG. 8, the receiver 24 captures the echo pulse waves created as a result of the ultrasonic frequency pulses contacting and being reflected by the target 13. The echo pulses in digitized form are transmitted to the computer along with digitized information about the frequencies of the original ultrasonic pulses. The operator identifies a region of interest within the patient using controls on the panel 16, the image displayed on the device 34, and a grid-like overlay over the displayed image. Cursors displayed on the device 34 act as X-axis ("X") and Y-axis ("Y") pointers. The cursors may be controlled by suitable controls on the panel 16.

After a region of interest has been determined, the computer scans the frequency data for the echo pulses to determine reflection peak positions and interpeak distances. Thereafter, the computer compares the peak slopes for the same peak at each different frequency. If the slopes are equal or within about 10% of each other, the computer proceeds to the next step in the process. If the slopes are not equal or are more than about 10% apart, the computer discontinues the analysis and increments or moves the Y cursor or pointer to the next Y position.

If the slopes of the same peak are equal or within about 10% of each other, the computers analyzes the pulses containing that peak to see if they are free of any anomalies such as shape irregularities. If the pulses are not free of anomalies, the computer again discontinues the analysis and increments the Y cursor to the next Y position.

If the pulses are free of anomalies at the first peak, the computer analyzes the same peak in the respective echo signals to see if the registered times of the rising peaks are within the period of the lower frequency. If the registered times are not within the period of the lower frequency, then the computer again discontinues the analysis and increments the Y cursor to the next Y position.

If the registered times are within the period of the lower frequency, the computer then analyzes the echo pulses containing the first peak to see if the width of each echo pulse at 3 dB below the peak is within about 10% of each other. If the widths are not within the desired range, the computer again discontinues the analysis and increments the Y cursor to the next Y position.

If the widths are within the desired range, the data information about the first peaks is saved as peak 1. The pointer is then moved and the next peak is compared for slope, anomalies, registered time and width as above. If the process is successfully completed, the next peak is saved as peak 2. The computer through its programming repeats the process for each peak in the echo pulses.

If none of the peaks in the echo pulses have slope differentials out of the desired range, shape anomalies, widths within the desired range and the desired time registration, the computer determines through its programming, in the case of two frequencies, the differential attenuation coefficient(s) for the various layers in the tissue matter being analyzed. After determining the Beta coefficients in the case of three frequencies, the computer using software containing certain mathematical relationships and equations determines the exponents of attenuation and the attenuation coefficients of the tissue matter being analyzed.

If the second or any subsequent peak in the echo pulses does not pass the above criteria, the computer as before increments the pointer to the next Y position.

As shown in FIG. 8, after the beta value(s) and/or attenuation coefficient(s) have been determined in the first Y position, the pointer is moved to the next Y position, preferably at an end of the region of interest where the foregoing process is repeated. To provide a complete picture of the tissue matter under examination, the process is repeated for a number of different positions along a Y-axis and a number of different positions along an X-axis transverse to the Y-axis.

After all of the beta value(s) and attenuation coefficients have been determined, a display of the data may be presented in any desired form. For example, there could be a print-out of the data or a display of an image of the tissue matter with the beta value(s) and attenuation coefficient(s) superimposed thereon. Also an image could be presented in different colors with different colors representing different attenuation coefficients.

If desired, the apparatus 10 may include a multifrequency phase analyzer to restore the magnitudes of the echo signals that is to determine compensation values for signals with slight irregularities about 10%.

As can be seen from the foregoing discussion the inventor has described an apparatus and a method for non-invasively determining a type of tissue or the state of such tissue. The method comprises the steps of using an imaging technique, preferably a B-mode two dimensional imaging device, to generate an image of the tissue matter to be analyzed; selecting a region of interest on said image; positioning a transducer for transmitting ultrasonic signals at desired frequencies in a desired location relative to the tissue matter to be analyzed; transmitting ultrasonic signals at different frequencies through the region of interest; detecting echo signals at said different frequencies; and analyzing the echo signals to determine at least one attenuation coefficient for said tissue matter. The method may be performed using ultrasonic signals at discrete frequencies, broad-band signals, or multiple pairs of signals. The method may also be performed using ultrasonic signals at three discrete frequencies. Still further, the ultrasonic signals may be transmitted simultaneously with, alternately with, or sequentially with the imaging signals.

The echo signals may be analyzed in either a manual mode or an automatic mode. In the manual mode, the echo pulses are visually displayed and examined to determine if the pulses are aligned in time and have any shape irregularities, any width variations and sufficient amplitude. When a set of frequencies have been found with pulses aligned in time and having no shape irregularities, no width variations and sufficient amplitude, the pulse waves are then used to determine at least one attenuation coefficient for said tissue matter using known mathematical techniques. In the automatic mode, analysis of the echo signals is performed by a pre-programmed computer.

While the invention has been described as having an A-mode display of frequencies, it should be recognized that different displays could be used in lieu thereof. For example, the display could be a ratio of frequency amplitudes.

While the method and apparatus of the present invention has been described in the context of determining the nature of tissue matter in a living entity and the state of that tissue matter, the method and apparatus has broader utility. The same method and apparatus could be used in fields such as metallurgy, geophysical testing and exploration, radiolocation, seismology, and any other field where an examination of an object can take place using any type of wave which has a dependency between energy attenuation and frequency. For example, the method and apparatus could be used to examine earthen material such as soil and rock formations. In some of these applications, the steps of generating an image of the matter being examined and selecting a region of interest may be omitted. Furthermore when the method and apparatus are used in these fields, the approximate 2% frequency difference for determining the use of the manual vis-a-vis the automatic mode of operation may be changed depending upon the application.

It is apparent that there has been provided in accordance with this invention a method and apparatus for non-invasively determining a type of tissue matter and/or its state within a living entity which fully satisfies the objects, means and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A method for non-invasively determining a type of tissue or a state of a tissue in a living entity comprising the steps of:
   (a) using an imaging technique to generate an image of the tissue matter to be analyzed;
   (b) selecting a region of interest on said image of said tissue matter to be analyzed;
   (c) positioning a device for transmitting an ultrasonic signal at a desired frequency in a desired location relative to said tissue matter to be analyzed;
   (d) transmitting a first ultrasonic signal at a first frequency through said region of interest using said device;
   (e) transmitting a second ultrasonic signal at a second frequency through said region of interest using said device;
   (f) detecting echo signals at said first and second frequencies reflected by said tissue matter; and
   (g) analyzing said echo signals to determine at least one attenuation coefficient for said tissue matter.

2. The method of claim 1 wherein said analyzing step comprises:
   comparing said echo signals to determine if pulses in said echo signals are aligned in time; and
   analyzing said reflected signals to determine if the pulses have any irregularities.

3. The method of claim 2 further comprising:
   (h) repositioning said device relative to said tissue matter if said pulses are misaligned or have any irregularities; and
   (i) repeating steps (c)-(g).

4. The method of claim 1 wherein said imaging step comprises generating a two dimensional (B-mode) image of said tissue matter to be analyzed and using said two dimensional image to determine the depth of said region of interest.

5. The method of claim 4 wherein said B-mode imaging step is performed simultaneous with said ultrasonic signal transmitting steps so as to substantially avoid anomalies caused by breathing or movement of said living entity.

6. The method of claim 4 wherein said B-mode imaging step is performed sequentially with said ultrasonic signal transmitting steps.

7. The method of claim 4 wherein said B-mode imaging step is performed alternately with said ultrasonic signal transmitting steps.

8. The method of claim 1 further comprising determining at least one of the nature of said tissue matter being examined and the state of said tissue matter being examined from said at least one attenuation coefficient.

9. The method of claim 1 wherein said analyzing step comprises:
   (j) matching the echo signals from a time standpoint;
   (k) maximizing the amplitude of the reflected signals;
   (l) matching the echo signals from a shape standpoint in order to compare pulse shapes; and
   (m) matching the echo signals from a width standpoint in order to compare pulse widths.

10. The method of claim 1 wherein said analyzing step further comprises determining frequencies from said echo signals at which errors are minimized.

11. The method of claim 1 further comprising transmitting said first and second ultrasonic signals sequentially.

12. The method of claim 1 further comprising:
    said transmitting steps comprising applying said first and second ultrasonic signals as a first two-frequency pair; and
    thereafter transmitting ultrasonic signals at a second pair of frequencies through said region of interest.

13. The method of claim 12 wherein said transmitting steps comprises transmitting said ultrasonic signals as broad-band signal.

14. The method of claim 12 wherein said second pair of frequencies transmitting step comprises transmitting a signal pair having one frequency which is in said first two-frequency pair.

15. The method of claim 1 further comprising transmitting a third ultrasonic signal at a third frequency through said region of interest spot, said third frequency being different from said first and second frequencies.

16. The method of claim 15 wherein said first, second and third signal transmitting steps comprise transmitting one broad-band signal and separating said first frequency, second frequency and third frequency signals therefrom.

17. The method of claim 15 wherein said analyzing step comprises simultaneously displaying echo signals at said first, second and third frequencies on a visual display device.

18. The method of claim 17 wherein said analyzing step further comprises determining a set of differential attenuation coefficients from said echo signals and thereafter determining said at least one attenuation coefficient from said set of differential attenuation coefficients.

19. The method of claim 1 wherein said transmitting steps comprises transmitting said ultrasonic signals as one broad-band signal and separating said signals from said one broad-band signal.

20. The method of claim 1 wherein said analyzing step is performed automatically by a computer if said frequencies are within about 2% of each other.

21. The method of claim 1 wherein said analyzing step comprises simultaneously displaying said echo signals with at least one signal having a "+ polarity" and at least one other signal having a "− polarity" on a visual display device.

22. An apparatus for non-invasively determining the nature of tissue matter within a patient and/or the state of said tissue matter, said apparatus comprising:
    means for generating an image of said tissue matter;
    means for selecting a region of interest on said generated image of said tissue matter to be analyzed;
    a transducer for transmitting ultrasonic signals having at least two different frequencies through said region of interest;
    means for detecting echo signals created by ultrasonic signals at said different frequencies passing through and being reflected by said tissue matter; and
    means for analyzing said echo signals at said different frequencies and determining at least one attenuation coefficient for said tissue matter from the analysis of said echo signals.

23. The apparatus of claim 22 wherein said imaging means comprises means for creating a two-dimensional image.

24. The apparatus of claim 23 wherein said transducer is used to transmit ultrasonic signals for generating said two-dimensional image.

25. The apparatus of claim 22 wherein said analyzing means includes means for visually displaying said echo signals.

26. The apparatus of claim 25 wherein said visual display means comprises an A-mode display device.

27. The apparatus of claim 25 further comprising;
a pulse generator for generating a first ultrasonic pulse at a first frequency and a second ultrasonic pulse at a second frequency, said second frequency being different than from said first frequency; and
said visual display means simultaneously displaying echo pulses at said first and second frequencies.

28. The apparatus of claim 27 wherein said pulse generator generates a third ultrasonic pulse at a third frequency and said visual display means simultaneously displaying echo pulse waves at each of said first, second and third frequencies.

29. The apparatus of claim 27 wherein said pulse generator generates said first and second pulses as one broad-band signal.

30. The apparatus of claim 27 wherein said pulse generator generates said pulses as a multi-frequency pair.

31. The apparatus of claim 22 further comprising:
means for converting said echo pulse signals from analog signals into digital signals; and
said analyzing means including programmed computer means for determining said attenuation coefficients from said digital echo pulse signals.

32. The apparatus of claim 22 further comprising:
a control panel unit for allowing an operator to select said region of interest on said image generated by said generating means and for selecting the frequencies at which said transducer generates said ultrasonic pulses.

33. The apparatus of claim 32 further comprising:
said control panel having switch means for allowing said operator to transmit said ultrasonic signals simultaneous with said image generation, in sequence with said image generation, or alternative with said image generation.

34. A method for non-invasively determining a type of matter or a state of said matter comprising the steps of:
(a) using an imaging technique to generate an image of the matter to be analyzed;
(b) selecting a region of interest on said image of said matter to be analyzed;
(c) positioning a device for transmitting a wave signal at a desired frequency in a desired location relative to said matter to be analyzed;
(d) transmitting a first wave signal at a first frequency through said region of interest using said device;
(e) transmitting a second wave signal at a second frequency through said region of interest using said device;
(f) detecting echo signals at said first and second frequencies reflected by said matter; and
(g) analyzing said echo signals to determine at least one attenuation coefficient for said matter.

35. An apparatus for non-invasively determining the nature of matter and/or the state of said matter, said apparatus comprising:
means for generating an image of said matter;
means for selecting a region of interest on said generated image of said matter to be analyzed;
means for transmitting wave signals at desired frequencies through said region of interest;
means for detecting echo signals created by said wave signals passing through and being reflected by said matter; and
means for analyzing said echo signals and determining at least one attenuation coefficient for said matter from the analysis of said echo signals.

36. A method for non-invasively determining a type of earthen material or a state of said material comprising the steps of:
(a) positioning a device for transmitting a wave signal at a desired frequency in a desired location relative to said material to be analyzed;
(b) transmitting a first wave signal at a first frequency through said material using said device;
(c) transmitting a second wave signal at a second frequency through said material using said device;
(d) detecting echo signals at said first and second frequencies reflected by said material; and
(e) analyzing said echo signals to determine at least one attenuation coefficient for said material.

* * * * *

UNITED STATES PATENT AND TRADEMARK OFFICE
CERTIFICATE OF CORRECTION

PATENT NO. : 5,361,767
DATED : November 8, 1994
INVENTOR(S) : IGOR YJKOV

It is certified that error appears in the above-indentified patent and that said Letters Patent is hereby corrected as shown below:

IN COLUMN 18, CLAIM 36, LINE 40, DELETE "A FIRST".

IN COLUMN 18, CLAIM 36, LINE 40, DELETE "SIGNAL AT A FIRST FREQUENCY" AND INSERT —SIGNALS HAVING AT LEAST TWO FREQUENCIES— IN ITS PLACE.

IN COLUMN 18, CLAIM 36, DELETE LINES 42 AND 43 IN THEIR ENTIRETY AND INSERT THE FOLLOWING IN ITS PLACE:
—(C) DETECTING ECHO SIGNALS HAVING AT LEAST TWO DIFFERENT FREQUENCIES REFLECTED BY SAID MATERIAL; AND—.

IN COLUMN 18, CLAIM 36, DELETE LINES 44 AND 45 IN THEIR ENTIRETY.

IN COLUMN 18, CLAIM 36, LINE 46, DELETE "(E)" AND INSERT —(D)— IN ITS PLACE.

Signed and Sealed this

Fifteenth Day of August, 1995

Attest:

BRUCE LEHMAN

*Attesting Officer*     *Commissioner of Patents and Trademarks*